(12) United States Patent
Paolizzi et al.

(10) Patent No.: US 8,000,812 B2
(45) Date of Patent: Aug. 16, 2011

(54) ELECTROSTIMULATION FACE MASK

(75) Inventors: Marco Paolizzi, Rimini (IT); Marco Valentini, Torre Pedrera (IT)

(73) Assignee: Vupiesse Italia S.R.L., Rimini (IT)

( * ) Notice: Subject to any disclaimer, the term of this patent is extended or adjusted under 35 U.S.C. 154(b) by 468 days.

(21) Appl. No.: 12/091,996

(22) PCT Filed: Nov. 17, 2005

(86) PCT No.: PCT/IT2005/000669
§ 371 (c)(1),
(2), (4) Date: Jul. 23, 2008

(87) PCT Pub. No.: WO2007/057930
PCT Pub. Date: May 24, 2007

(65) Prior Publication Data
US 2008/0281392 A1    Nov. 13, 2008

(51) Int. Cl.
*A61N 1/04*    (2006.01)
(52) U.S. Cl. ..................................................... 607/140
(58) Field of Classification Search .................. 607/140, 607/74, 50, 76, 145–151
See application file for complete search history.

(56) References Cited

U.S. PATENT DOCUMENTS

| | | | | |
|---|---|---|---|---|
| 5,067,478 A | * | 11/1991 | Berlant | 601/15 |
| 5,357,957 A | * | 10/1994 | Itil et al. | 600/383 |
| 5,527,357 A | * | 6/1996 | Springer, Jr. | 607/140 |
| 6,181,974 B1 | * | 1/2001 | Springer, Jr. | 607/140 |
| 2004/0252104 A1 | | 12/2004 | Nakamura et al. | |

FOREIGN PATENT DOCUMENTS

| | | |
|---|---|---|
| EP | 0603451 A | 6/1994 |
| GB | 15634 A | 2/1911 |
| JP | H033356 U | 1/1991 |
| JP | 05146515 A | 6/1993 |
| RU | 0093058217 | 12/1993 |
| SU | 1502030 A1 | 8/1989 |
| SU | 1572626 A1 | 6/1990 |

OTHER PUBLICATIONS

Klyachkin L. M., et al., "Physiotherapy", M.: Meditsina, 1988, p. 69, English translation enclosed.

* cited by examiner

*Primary Examiner* — Carl H Layno
*Assistant Examiner* — Paula J Stice
(74) *Attorney, Agent, or Firm* — Pearne & Gordon LLP

(57) ABSTRACT

An electrostimulation device comprises at least one shell (2) forming an inner compartment (21) and comprising an opening (22); at least one electrode (3) located at least partly outside the corresponding shell (2) at the opening (22). The device is characterised by the fact that the electrode (3) is connected to an articulated joint (4). The articulated joint (4) is at least partly inside the shell (2) and mobile in its seat (41). The electrode (3) can be angled and moved relative to the shell (2) as a result of the freedom of movement of the articulated joint (4) in its seat (41) depending on the anatomical form and structure of the treatment zone (8).

21 Claims, 5 Drawing Sheets

ELECTROSTIMULATION FACE MASK

TECHNICAL FIELD

The present invention relates to a muscular electrostimulation device and a face mask comprising said device.

Muscular electrostimulation devices are normally used to allow the passive exercising of muscles in many areas of the human body. In particular, the present invention is advantageously used in the treatment of facial muscles to recover muscle tone and combat the signs of ageing.

BACKGROUND ART

Muscular electrostimulation devices of the type described in patent document EP0603451 are known. Such devices comprise an outer case with a pair of electrodes and a handgrip. The case has a seat with an opening for each of the electrodes. In the home position said opening is blocked by the electrode held in position by a helical spring, whilst the seat contains a conducting liquid. After pressure is applied to the electrode by the area of the patient being treated, the resistance of the spring is overcome. As a result, the electrode moves and the liquid originally in the seat flows out, wetting the skin and improving electrical conductivity.

The muscular electrostimulation devices described above have several disadvantages.

In particular, at dips or bumps on the face, the pair of electrodes described above are unable to precisely follow the outline of the surfaces of the body being treated. Poor electrical contact between the electrode and the surface being treated results in the user feeling discomfort, pain and in extreme cases forms of skin burns.

Devices are also known which use electrodes and adhesive gels which are expensive and inconvenient on the face because they do not allow any movement once positioned. The gel is also expensive and dirties the zone treated.

DISCLOSURE OF THE INVENTION

The aim of the present invention is to overcome the above-mentioned disadvantages by providing a muscular electrostimulation device which allows the patient to avoid pain, discomfort and burns.

Another aim of the present invention is to provide an electrostimulation device which allows the plurality of electrodes to follow the outline of the surface to be treated even in critical zones such as dips or bumps on the human body.

Yet another aim of the present invention is to provide a face mask comprising said electrostimulation device, the mask being particularly convenient to use.

These aims and others, which are more apparent in the description which follows, are achieved, in accordance with the present invention, by an electrostimulation device with the structural and functional characteristics described in the independent claims herein. Alternative embodiments of the device are described in the dependent claims.

BRIEF DESCRIPTION OF THE DRAWINGS

The invention is described in more detail below, with reference to the accompanying drawings, which illustrate a preferred non-limiting embodiment of the invention, and in which.

DETAILED DESCRIPTION OF THE PREFERRED EMBODIMENTS OF THE INVENTION

Figure 1:
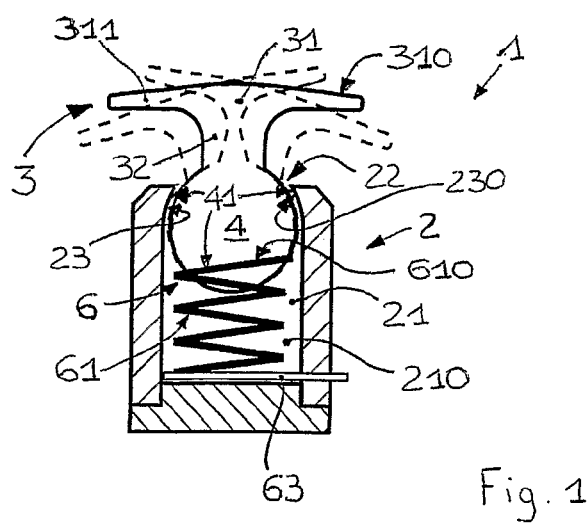
FIG. 1 is a cross-section of the device in accordance with the invention.

The following description is supplied by way of example and is non-limiting.

With reference to the accompanying drawings, the numeral 1 denotes a muscular electrostimulation device of the type comprising at least one shell 2. The shell 2 has an inner compartment 21. The shell 2 also comprises at least one opening 22. The inner compartment 21 preferably has the shape of a cylindrical chamber 210 which tends to have a smaller cross-section at the opening 22. The opening 22 is preferably positioned at one end of the shell 2. In particular, the opening 22 is positioned at a base of the cylindrical chamber 210. The electrostimulation device 1 also comprises at least one electrode 3. The electrode 3 is located at least partly outside the shell 2 at the opening 22.

Figure 9:
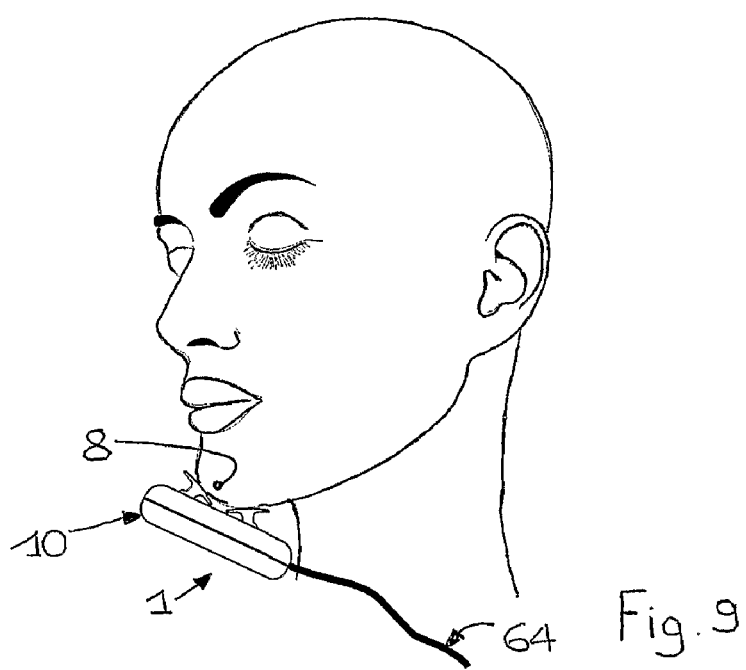

The device is characterised by the fact that each electrode 3 is connected to an articulated joint 4. The articulated joint 4 constitutes an articulated connection between the electrode 3 and the shell 2 in such a way that the electrode 3 and the shell 2 can move relative to one another without any loss of cohesion. The articulated joint 4 is at least partly inside the shell 2. The articulated joint 4 is also mobile in its own seat 41. The electrode 3 can be angled and moved relative to the shell 2 as a result of the freedom of movement of the articulated joint 4 in its seat 41, depending on the anatomical form and structure of the treatment zone 8. In particular, according to a preferred but non-limiting configuration, the electrostimulation device 1 comprises at least one pair of electrodes 3 and corresponding shells 2. This is illustrated for example in FIGS. 2, 4, 5, 6. In this configuration a case 10 connects the shells 2 of the various electrodes 3. The various electrodes 3 brought into contact with the patient's treatment zone 8 allow the electrical circuit to be made. This electrical circuit is connected to a voltage or current generator. Advantageously, the electrical current generated is an alternating pulsing current. As illustrated in FIG. 9, even close to dips or bumps on the face such as the chin, jaws, arch of the eyebrows, forehead, the electrostimulation device 1 allows optimisation of the contact between each electrode 3 and the treatment zone 8. However, the muscular electrostimulation device 1 can also be used on parts of the body other than the face.

The electrode 3 comprises a first portion 31 which during use is located close to the treatment zone 8. The electrode 3 also comprises a second portion 32 which connects the first portion 31 to the articulated joint 4.

Advantageously, the electrode 3 is shaped like a mushroom. The first portion 31 corresponds to the mushroom cap. The second portion 32 corresponds to the mushroom stalk. As illustrated in the accompanying drawings, the first portion 31 comprises a plate-shaped head 311.

The first portion 31 comprises a first surface 310 which during use is opposite the treatment zone 8. Said first surface 310 is advantageously dome-shaped. Alternatively, the first surface 310 could also be flat.

In the embodiments illustrated the electrode 3 could form part of a single body with the articulated joint 4.

In an alternative configuration, the electrode 3 is removably connected to the articulated joint 4, for example by a threaded connection. In this way, the electrode 3 can be removed and substituted with another electrode 3 specially shaped to allow treatment of a particular zone of the face or body.

The articulated joint 4 and the electrode 3 are made of a material which conducts electricity. The electrode 3 is advantageously made of stainless steel or nickel-plated brass.

The first surface 310 is covered by a spongy element 5 which is soaked before each treatment to give it good electrical conductivity. Advantageously, said spongy element 5 is soaked in water or in another liquid which conducts electricity. The spongy element 5 is preferably made of pure cellulose, an ideal material for holding water without causing any type of skin allergy.

The use of water is particularly advantageous both in terms of inexpensiveness and because it does not dirty the treatment zone 8.

The spongy element 5 is removably connected to the first portion 31 of the electrode 3.

The spongy element 5 is preferably irremovably connected to a support 51 for connection to the first portion 31 of the electrode 3. The support 51 is preferably made of PVC foam. The spongy element 5 and the support 51 are suitably coupled by industrial bonding techniques.

Figure 2:
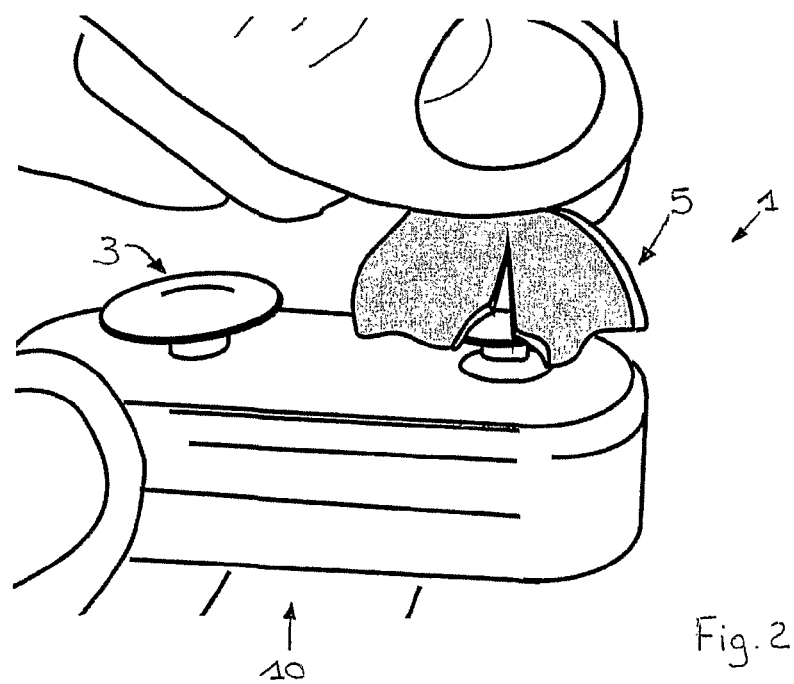
FIG. 2 is a perspective view of the device in accordance with the invention.
Figure 3:
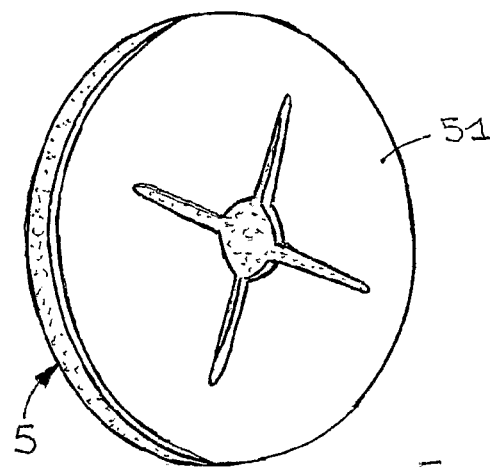
FIG. 3 is a perspective view of a construction detail illustrated in FIG. 2.
Figure 4:
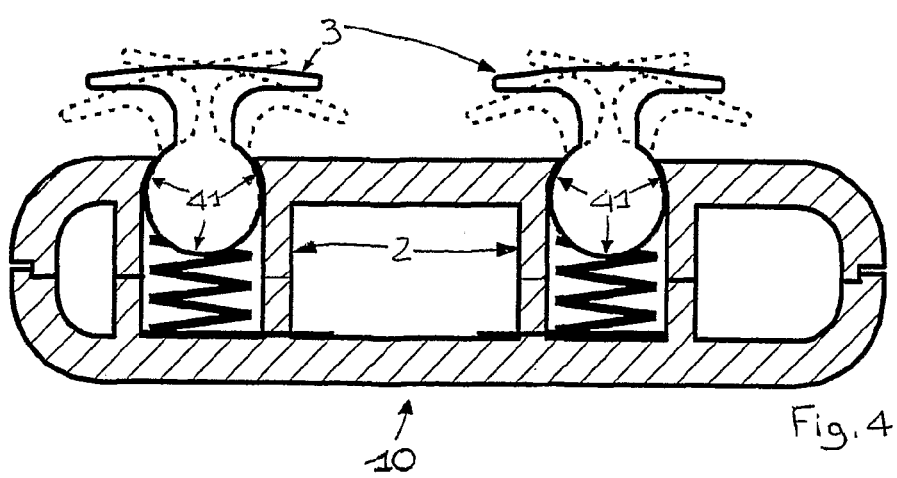
FIG. 4 is a longitudinal section of the device illustrated in FIG. 2.
Figure 5:
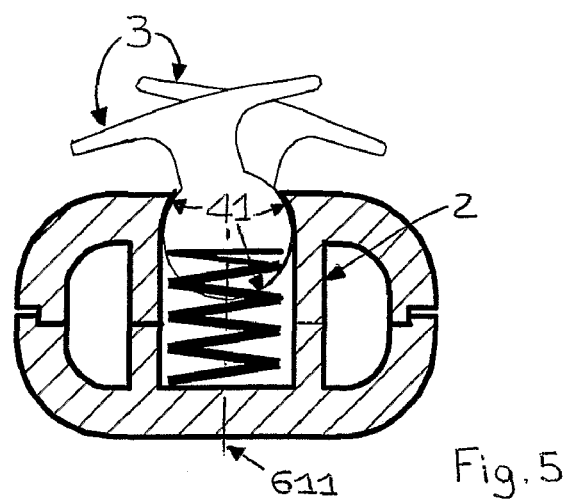
FIG. 5 is a cross-section of the device illustrated in FIG. 2.
Figure 6:
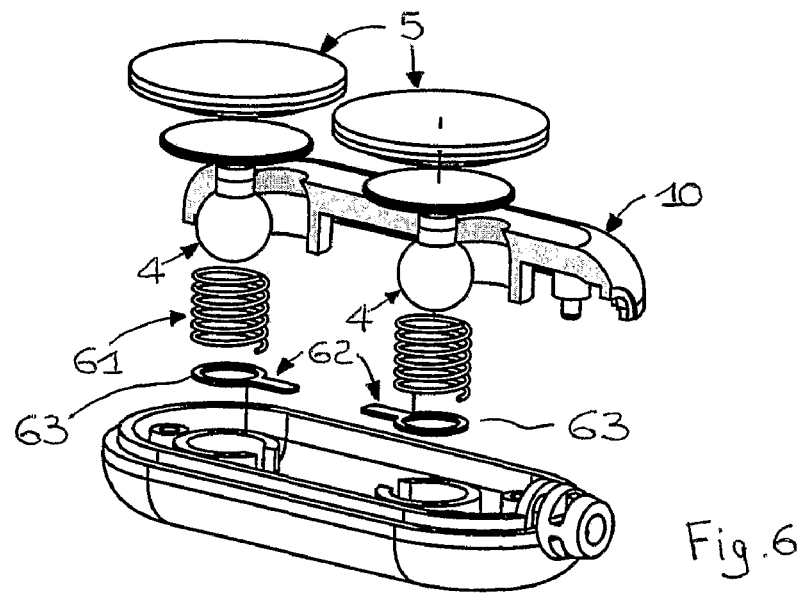
FIG. 6 is an exploded view of the device illustrated in FIG. 2.

The support 51 is suitably punched so that it surrounds the first portion 31 of the electrode 3 as illustrated in FIGS. 2 and 3.

The spongy elements 5 are periodically substituted when dirty or worn.

Thanks to the support 51, the spongy element 5 can be substituted easily and rapidly. The spongy element 5 is also shaped in such a way that it allows a large contact surface with the skin, thus improving treatment comfort.

The relatively low cost of the spongy element 5 and the support 51 relative to the entire electrostimulation device 1 also allows their substitution every time the electrostimulation device 1 is used by a new patient. This makes it hygienic.

The electrostimulation device 1 comprises elastic means 6 in the compartment 21 which elastically suspend the articulated joint 4.

The elastic means 6 comprise a helical spring 61. The helical spring 61 is made of a material which conducts electricity, preferably metal. The helical spring 61 has a longitudinal axis 611. When the skin of the treatment zone 8 is simply pressed, the articulated joint 4 can slide in the compartment 21, compressing the elastic means 6, in particular the helical spring 61. For each electrode 3, the electrostimulation device 1 comprises a conductor element 62 located in contact with the helical spring 61. The helical spring 61 is in turn in electrical contact with the electrode 3 by means of the articulated joint 4. The conductor element 62 preferably comprises a ring 63 to which a lead 64 is connected, in turn connected to the electricity supply 65.

The seat 41 is at least partly formed by an inner surface 23 of the shell 2 close to the opening 22.

The seat 41 is at least partly formed by a coil 610 of the helical spring 61 closest to the opening 22.

The articulated joint 4 can rotate freely through 360° about the longitudinal axis 611 of the helical spring 61. Consequently the electrode 3 can also rotate freely through 360° about the longitudinal axis 611 of the helical spring 61.

As illustrated in FIGS. 1, 4, 5, 6 the articulated joint 4 is, advantageously, a ball joint.

The inner surface 23 of the shell 2, close to the opening 22 forms a contact surface 230 for the articulated joint 4. The articulated joint 4 is, advantageously, pressed against said contact surface 230 by the helical spring 61. The contact surface 230 consists of a surface shaped to match the articulated joint 4 and converging towards the longitudinal axis 611 of the spring 61. The articulated joint 4 is preferably a ball joint and the opening 22 is circular. In such a case the diameter of the opening 22 is smaller than the diameter of the articulated joint 4 ball.

Advantageously, the electrode 3 is shaped according to a symmetrical axis. The electrode 3 may be moved in an operating cone. The vertex of the cone coincides with the centre of rotation of the articulated joint 4. The maximum angle of opening of said cone is determined by the contact between the second portion 32 of the electrode 3 and the contact surface 230 of the shell 2.

Figure 7:
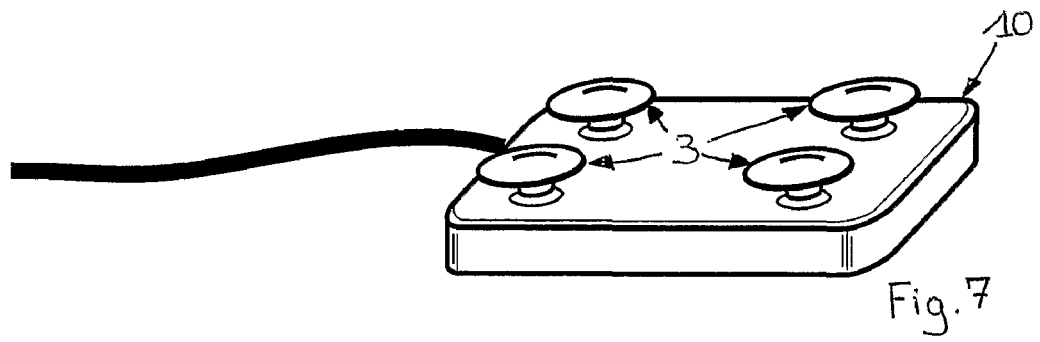
FIG. 7 is a perspective view of another configuration of the device in accordance with the invention.
Figure 8:
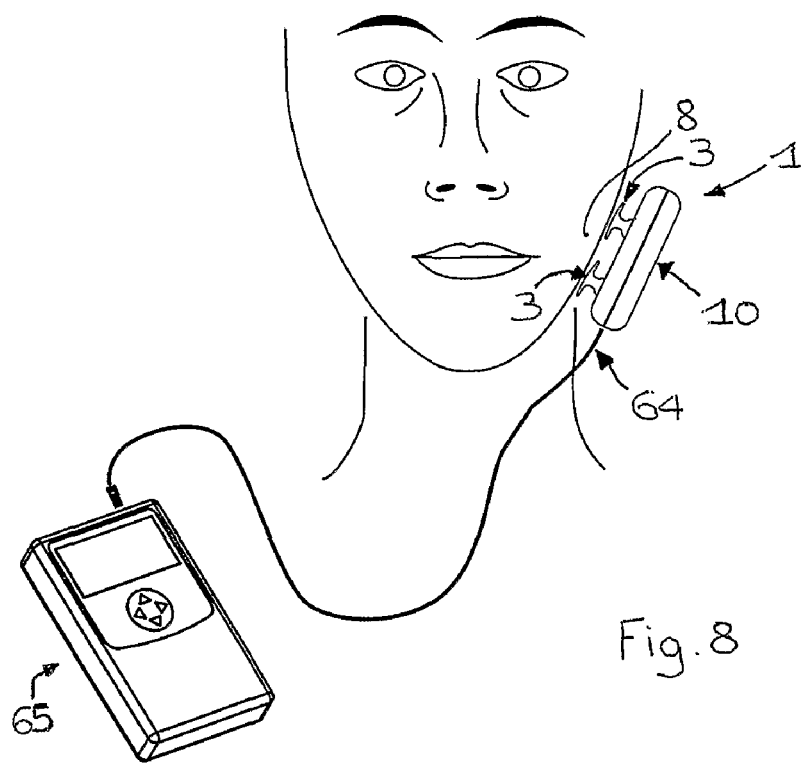
FIGS. 8 and 9 are views of two examples of application of the device in accordance with the invention illustrated in FIG. 2.

As illustrated in FIG. 7, the electrostimulation device 1 comprises a plurality of electrodes 3, of the type previously described, which can be applied on the treatment zone 8. In particular in FIG. 7 the electrostimulation device 1 comprises four electrodes 3 connected to the same case 10.

Figure 10:
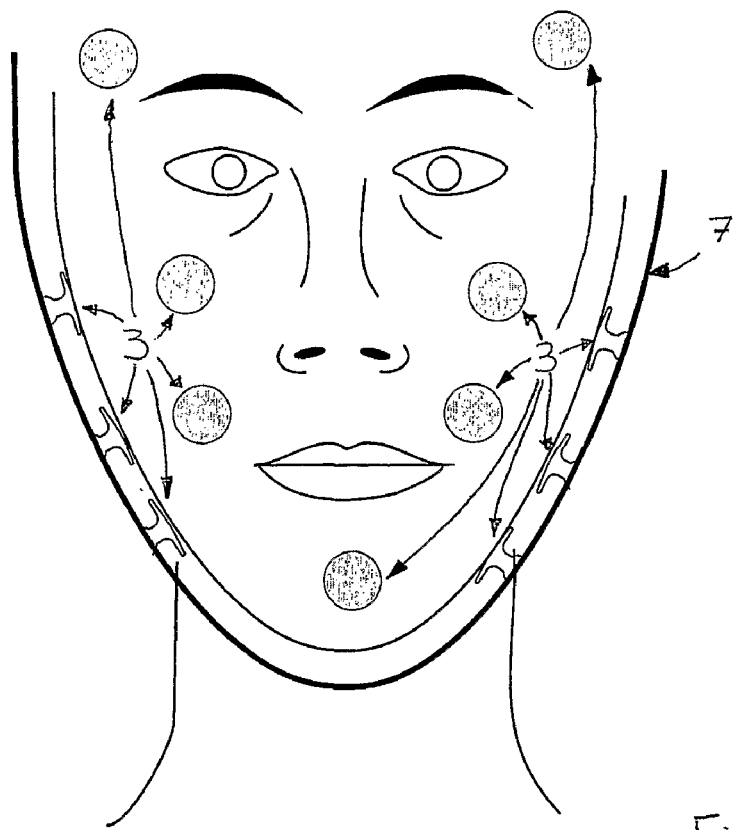
FIGS. 10 and 11 illustrate further configurations of the device in accordance with the invention.
Figure 11:
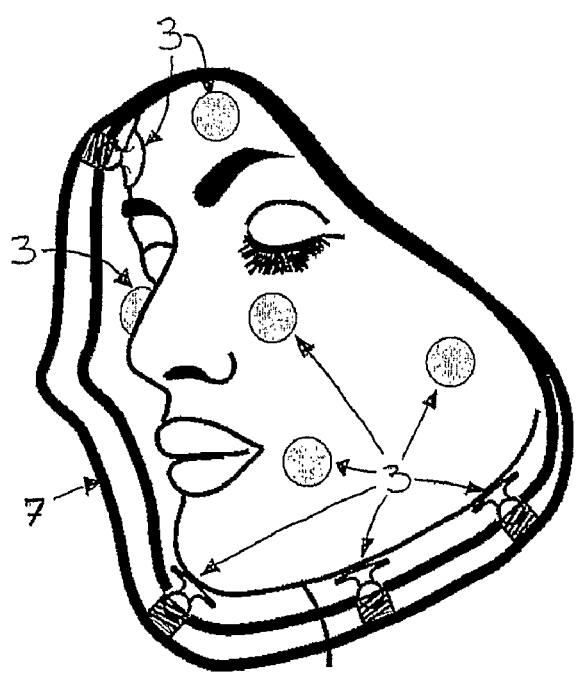

FIGS. 10 and 11 illustrate a face mask 7 comprising a plurality of electrostimulation devices 1 of the type previously described. In this way, each electrode 3 is positioned at the muscles of a specific area of the face. Advantageously, the mask 7 is transparent. In this way, the electrodes 3 can be precisely positioned by an external operator on the points of application requested by the patient. To facilitate this operation, advantageously, the mask 7 comprises handgrips (not illustrated in FIGS. 10 and 11) at each electrode 3. The mask 7 electrodes 3 can be arranged in pairs. In another configuration there is a plurality of electrodes 3 operating in sequence, sending electrical pulses. By operating these electrodes 3 in sequence, one after another, the mask 7, in each portion corresponding to half of the face, advantageously comprises only one shared electrode 3 having the function of making the electrical circuit.

The invention brings important advantages.

Firstly, the device allows patients to avoid discomfort, pain or skin necrosis.

Secondly, it allows uniform treatment of the various zones of the body, even those where there are dips or bumps. The complete mobility in all directions of the electrode 3 allows it to adapt to the shape of the area treated.

Another important advantage is the maximum hygiene linked to interchangeability of the spongy element which makes contact with the patient's skin.

The invention described may be modified and adapted without thereby departing from the scope of the inventive concept.

Moreover, all details of the invention may be substituted by other technically equivalent elements.

In practice, all of the materials used, as well as the dimensions may be any, according to requirements.

The invention claimed is:

1. An electrostimulation device of the type comprising:
   at least one shell (2) forming an inner compartment (21), the shell (2) comprising at least one opening (22);
   at least one electrode (3) located at least partly outside the corresponding shell (2) at the opening (22);

wherein the electrode (3) is connected to an articulated joint (4) and wherein the articulated joint (4) is at least partly inside the shell (2) and mobile in its seat (41), wherein the articulated joint is a ball joint, wherein the electrostimulation device also comprises, inside said inner compartment, a helical spring which elastically suspends the ball joint, and wherein the seat is partly formed by an inner surface of the shell close to the opening and partly formed by a coil of said helical spring closest to the opening, allowing the electrode (3) to be angled and moved relative to the shell (2) as a result of freedom of movement of the articulated joint (4) in its seat (41) depending on anatomical form and structure of a treatment zone (8).

2. The electrostimulation device according to claim 1, characterised in that the electrode (3) comprises a first portion (31) which during use is located close to a surface to be treated and a second portion (32) which connects the first portion (31) to the articulated joint (4).

3. The electrostimulation device according to claim 2, characterised in that the electrode (3) is shaped like a mushroom, the first portion (31) corresponding to a mushroom cap and the second portion (32) corresponding to a mushroom stalk.

4. The electrostimulation device according to claim 3, characterised in that the first portion (31) comprises a first surface (310) which during use is opposite the treatment zone (8), the first surface (310) being dome-shaped.

5. The electrostimulation device according to claim 4, characterised in that the first surface (310) is covered by a spongy element (5) which is soaked before each treatment to give it good electrical conductivity.

6. The electrostimulation device according to claim 5, characterised in that the spongy element (5) is removably connected to the first portion (31) of the electrode (3).

7. The electrostimulation device according to claim 6, characterised in that the spongy element (5) is irremovably connected to a support (51) for connection to the first portion (31) of the electrode (3).

8. The electrostimulation device according to claim 7, characterised in that the support (51) is punched so that it surrounds the first portion (31) of the electrode (3).

9. The electrostimulation device according to claim 5, characterised in that the spongy element (5) is irremovably connected to a support (51) for connection to the first portion (31) of the electrode (3).

10. The electrostimulation device according to claim 9, characterised in that the support (51) is punched so that it surrounds the first portion (31) of the electrode (3).

11. The electrostimulation device according to claim 2, characterised in that the first portion (31) comprises a first surface (310) which during use is opposite the treatment zone (8), the first surface (310) being dome-shaped.

12. The electrostimulation device according to claim 11, characterised in that the first surface (310) is covered by a spongy element (5) which is soaked before each treatment to give it good electrical conductivity.

13. The electrostimulation device according to claim 12, characterised in that the spongy element (5) is removably connected to the first portion (31) of the electrode (3).

14. The electrostimulation device according to claim 13, characterised in that the spongy element (5) is irremovably connected to a support (51) for connection to the first portion (31) of the electrode (3).

15. The electrostimulation device according to claim 14, characterised in that the support (51) is punched so that it surrounds the first portion (31) of the electrode (3).

16. The electrostimulation device according to claim 12, characterised in that the spongy element (5) is irremovably connected to a support (51) for connection to the first portion (31) of the electrode (3).

17. The electrostimulation device according to claim 16, characterised in that the support (51) is punched so that it surrounds the first portion (31) of the electrode (3).

18. The electrostimulation device according to claim 1, characterised in that the electrode (3) is removably connected to the articulated joint (4).

19. The electrostimulation device according to claim 1, characterised in that the articulated joint (4) and the electrode (3) are made of a material that conducts electricity.

20. The electrostimulation device according to claim 1, comprising at least one pair of electrodes (3) and corresponding shells (2).

21. A face mask comprising an electrostimulation device (1) according to claim 1.

* * * * *